United States Patent [19]

Blackburn et al.

[11] Patent Number: 4,703,062

[45] Date of Patent: Oct. 27, 1987

[54] PARENTERAL NUTRITION WITH MEDIUM AND LONG CHAIN TRIGLYCERIDES

[75] Inventors: George L. Blackburn, Cambridge; Vigen K. Babayan, Waban; Bruce Bistrian, Ipswich, all of Mass.; Lyle L. Moldawer, Molndal, Sweden; Richard Cotter, Libertyville, Ill.

[73] Assignee: Baxter Travenol Laboratories, Inc., Deerfield, Ill.

[21] Appl. No.: 774,254

[22] Filed: Sep. 9, 1985

Related U.S. Application Data

[63] Continuation-in-part of Ser. No. 571,021, Jan. 16, 1984, abandoned.

[51] Int. Cl.⁴ .............................................. A21K 31/23
[52] U.S. Cl. .................................... 514/552; 514/893; 514/938
[58] Field of Search .................. 514/552, 893, 938

[56] References Cited

FOREIGN PATENT DOCUMENTS 0071995 6/1982 European Pat. Off. ............ 514/552

OTHER PUBLICATIONS

Eckart et al., J. Parent. and Ent. Nut. 4:(4):360–366, 1980.
Bach, et al., Am. J. Clin. Nut. 36:950–962, 1982.

*Primary Examiner*—J. R. Brown
*Assistant Examiner*—John W. Rollins, Jr.
*Attorney, Agent, or Firm*—Paul C. Flattery; Robert E. Hartenberger; Susan B. Fentress

[57] ABSTRACT

Medium chain triglyceride containing lipid emulsions for the nutrition of liver diseased or septicemic patients are improved by the inclusion in the emulsions of long chain triglycerides. The emulsions may also contain amino acids in proportions desirable for the nutrition of liver diseased patients, as well as carbohydrates, drugs, vitamins and electrolytes.

4 Claims, 8 Drawing Figures

PARENTERAL NUTRITION WITH MEDIUM AND LONG CHAIN TRIGLYCERIDES

This is a continuation-in-part of copending U.S. patent application Ser. No. 571,021 filed on Jan. 16, 1984, now abandoned.

BACKGROUND

This relates to total parenteral nutrition of patients with liver disease or septicemia. It is particularly concerned with providing such nutrition via lipid emulsions. Lipid emulsions for parenteral nutrition are available commercially or can be manufactured in accordance with known processes. Generally, such emulsions have been made using the triglycerides of long chain fatty acids (LCTs). LCTs are obtained conventionally from soybean or safflower oil. Long chain fatty acids are fatty acids having 14 or more carbon atoms, usually 16 or 18 carbon atoms.

More recently, lipid emulsions which contain triglycerides of medium chain fatty acids (MCTs) have become available. MCTs are triglyceride esters of fatty acids which contain a preponderance of $C_8$ and $C_{10}$ fatty acids (caprylic and capric acid, respectively). Emulsions of this type are disclosed in European Patent Application No. 0071995 and Eckart et al., "J. Parenteral and Enteral Nutrition" 4(4):360–366 (1980). The above cited European Patent Application discloses an isotonic LCT/MCT emulsion for parenteral use, which contains a fat content of 3 to 30%, an LCT/MCT ratio between 4/1 and ¼, a physiologically unobjectionable polyhydric alcohol and egg phosphatide as emulsifier.

Early studies involving enteral administration of MCT emulsions to animals and man indicated that MCTs are handled by a physiological pathway other than the one known for LCTs. In-depth studies revealed that MCTs are hydrolyzed to free fatty acids in the intestinal lumen at a rate five times faster than the hydrolysis rate for LCTs. Further, these MCT-derived fatty acids are absorbed by the intestinal cell at a rate twice the absorption rate of LCT-derived fatty acids. The most striking difference between MCT and LCT was shown to be the mechanism of transport to sites of utilization and, as a result, their predominant mode of utilization. MCT-derived fatty acids pass through the intestinal epithelial cell without reesterification to MCT. They then enter the portal vein, bind to albumin, and are transported in this bound form in the bloodstream. LCT-derived fatty acids, on the other hand, after absorption are reesterified in intestinal cells to form LCT and packaged with protein and phospholipids to form lipid particles (chylomicrons) that enter the lymph system and, later, the circulatory system for distribution to the tissues of utilization.

In comparison to LCTs, MCTs are much more readily utilized for caloric energy, but are less effectively incorporated into tissue lipids. MCTs, when administered orally, are believed to be metabolized primarily in the liver, while LCTs are metabolized throughout the body (Scheig, R. In: *Medium Chain Triglycerides*, J. R. Senior, Ed. pp 39–49 [1968]).

Liver disease as this term is used herein means a primary or secondary disorder of the liver parenchyma that results in reduced hepatic function. The etiology of the disease may include but not be limited to any one of the following common disorders: Alcoholic cirrhosis, acute hepatocellular damage secondary to drug abuse or poisoning, genetic deficiencies such as tyrosinosis, trauma to the liver, hepatitis, primary biliary cirrhosis, liver abscess, Budd-Chiari syndrome, Wilson's disease, or primary or secondary liver neoplasms. Clinically, hepatic dysfunction is diagnosed by increases in liver function tests such as serum glutamate-oxaloacetate transaminase, serum glutamate-pyruvate transaminase and bilirubin, reductions in indocyanin green or bromosulphopthalein clearance, tissue biopsy, and/or neurological manifestations such as encephalopathy. Liver disease as defined herein excludes the subclinically mild and reversible hepatic dysfunction induced by parenteral nutrition (Eckart et al. Ibid).

Patients with septicemia include patients having subclinical septicemia or susceptibility to septicemia. Patients in this group include patients recuperating from abdominal surgery, patients with respiratory diseases and those with active infections such as abcesses or infected wounds.

Intravenous calorie intake in liver diseased patients is hampered by chronic carbohydrate and fluid intolerance. In addition, current LCT emulsions, although calorically dense, are contraindicated in liver disease because liver dysfunction is frequently associated with an impaired ability to metabolize LCT. A need exists for an intravenous calorie source for liver diseased patients that does not exhibit the disadvantages of available calorie sources.

MCTs have been included in oral formulations for the nutrition of stressed (including liver disease) patients. An example is the Travasorb Hepatic formulation sold by Travenol Laboratories, Inc. The doses of MCT to be delivered with such formulations have been low, however, on the order of about 0.2 mg MCT/Kg body weight (BW)/min. when following the instructions for use. MCTs are added to these nutrient formulations because they are believed necessary to circumvent the maladsorption of LCTs that accompanies deficient bile secretion by diseased livers. However, the low doses were believed mandated by the prevalent belief in the art that MCTs are harmful to liver diseased patients. See, for example, N. Greenberger et al. "Ann. Intern. Med." 66(4):727–734 (1967), who state that "it will be important to withhold MCT therapy from patients with decompensated cirrhosis until more is known about the effects of MCT therapy on such patients." (Id at p. 732). In part, this contraindication is based on the role of the liver as the primary site of medium chain fatty acid metabolism. The dysfunctional liver might not be expected to metabolize these fatty acids at a rate sufficient to avoid the observed effects of excess fatty acids in the blood: Somnolence, vomiting and even death. In addition, the narcotic effect of MCTs could be expected to exacerbate any tendency in liver diseased patients towards encephalopathy. Thus, MCTs have not been considered appropriate for providing a substantial percentage of the calorie needs of liver diseased patients.

We now have discovered that MCTs can be parenterally administered to recipients with liver disease or septicemia, and in dosages heretofore believed to be potentially hazardous, without toxic side effects. We have found that MCTs can supply nutritionally adequate calories to such patients without resulting in the liver fatty deposits or the reductions in the efficacy of the reticuloendothelial system (RES) noted when supplying LCTs as a significant calorie source.

SUMMARY

The improvement herein comprises parenterally administering a composition comprising MCTs to a liver diseased patient or a patient with septicemia. It further comprises administering greater than about 0.35 mg MCTs/Kg BW/min. to such patients, preferably about from 0.5 to 2 mg MCTs/Kg BW/min., and selecting a weight proportion of MCTs to LCTs no greater than about 3 to 1.

The improvement herein also comprises compositions including (1) a composition comprising (a)lipids wherein about from 25% to 75% by weight of the lipids are MCTs and the remainder are LCTs and (b)the branched chain amino acids, valine, leucine and/or isoleucine or the keto analogues of valine, leucine and/or valine.

(2) a composition comprising MCTs and at least one branched chain amino acid, or preferably an amino acid mixture in which greater than about 35% of the mole weight of amino acids are valine, isoleucine and/or leucine or the keto analogues of valine, isoleucine and/or leucine.

DETAILED DESCRIPTION

Figure 1:
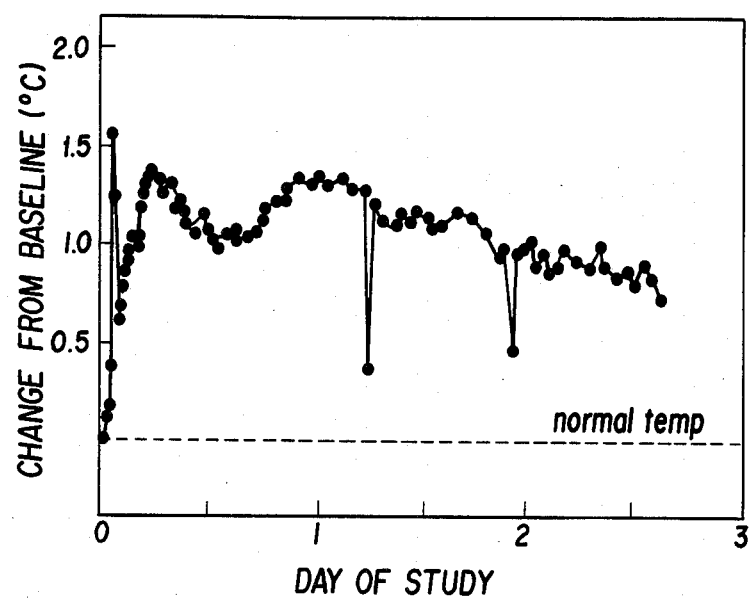
FIG. 1 relates to example 7 and illustrates the change in body temperature of the control rats of study I.

The MCTs to be used herein will be $C_6$, $C_8$, $C_{10}$ and/or $C_{12}$ mixtures in proportions ranging in weight percent about from 0% to 3%, 50% to 100%, 50% to 100%, and 0% to 3%, respectively. Usually only $C_8$ and $C_{10}$ fatty acids will be present, in ratios of about from 1:3 to 3:1. Preferably, the proportions $C_6$, $C_8$, $C_{10}$ and $C_{12}$ fatty acids will be §2%, 65–80%, 20–35%, and §2%. The MCT compositions can contain free fatty acids at up to about 0.005/mEq/g (USP), will have a saponification value of about from 325–365 (USP) and an iodine value (USP Method II) of up to about 1.0 gI$_2$/100 g. Color (Lovibond, AOCS Cc 13h.45) is preferably 1.0 R. Unsaponifiable matter (USP), hydroxyl value (USP), and heavy metals (USP Method II) should be less than about 1.0%, 10.0 and 10 ppm, respectively. The refractive index (USP) and specific gravity (USP) range from about 1.440 to 1.460 and 0.920 to 0.960, respectively. These specifications are not critical. MCT oils of this type are commercially available as lauric oils from coconut oil. The exact specifications, including the relative proportions of $C_6$ to $C_{12}$ medium chain fatty acids, will vary somewhat since the MCTs are obtained from natural sources.

The MCTs are used alone or incorporated with minor proportions of LCTs into the oil phase of an oil-in-aqueous emulsion. The proportion of MCTs to LCTS is preferably no more than about 3:1 by weight. However, emulsions containing MCTs as the sole lipid source are suitable for use at physiologic nonprotein calorie intakes for the nutrition of liver diseased patients. Animals having surgically induced liver disease (disclosed in Example 5 below) have shown no tendency towards somnolence or overt encephalopathic symptoms upon administration of MCTs at substantial proportions of normal, physiologic nonprotein calorie intakes. MCT dosages of up to about 4 mg MCTs/Kg/hr can be administered on a continuous basis, although the physician will need to tailor the maximum dose to the capabilities of the patient and be observant for toxicity symptoms such as vomiting and lethargy.

Studies with normal animals have disclosed that MCT toxicity can be ameliorated by supplying a proportion of non-protein calories as LCTs. A given hyperphysiological dose of MCTs may result in MCT toxicity symptoms, but the same dose accompanied by an approximately equal or minor proportion of LCTs will not produce the symptoms. Thus in the case of liver patients who exhibit various degrees of compromised MCT metabolic capacity, it is preferred that the MCT emulsions contain a proportion of LCTs, i.e., about from 15% to 50% by weight of the total lipids.

The MCT-containing emulsions may contain other substances besides LCTs. These include surfactants such as egg or soya phospholipid, tonicity adjusting agents such as glycerol, carbohydrate nutrients such as dextrose, and electrolytes, amino acids, vitamins and trace minerals. The concentration by weight of the oil in the emulsion is about from 5% to 20%, with 20% being preferred.

The amino acid compositions used in the aqueous phase of the emulsions for use with liver diseased patients preferably will have one or more of the following characteristics:

(a) The total mole percent of the amino acids serine, glycine, threonine, tryptophan, glutamine and histidine will range about from 8% to 16%;

(b) The total mole proportion of valine, leucine and isoleucine, (or their keto analogues α-ketoisovaleric, ketoisocaproic and α-keto-β-methyl valeric acid, respectively) to the other amino acids will be greater than about 35%, preferably about 40% to 60% and more optimally about 50%; and/or (c) A reduced proportion of sulfur-containing amino acids, e.g. methionine, when compared to standard formulations based on proteins such as egg white.

The amino acid compositions optimally will include essential and nonessential amino acids, in the latter group especially arginine and histidine. These last two amino acids are known to be desirable in the nutrition of liver diseased patients. A representative amino acid composition is disclosed in PCT International Application published as No. WO 83/00085. Other representative compositions that have been urged to be useful in the nutrition of liver diseased patients are disclosed in U.S. Pat. Nos. 3,950,529; 4,100,293; 3,832,465; and 4,259,353; and U.K. Pat. No. 2,037,161A, all of the foregoing being incorporated by reference. The amino acids are desirably supplied in the crystalline form rather than as protein hydrolysates. The amount of amino acids included in the emulsions will be sufficient to maintain patients' nitrogen requirements at the planned rate of infusion of MCT and/or LCT calories.

The lipid droplets in the emulsion will have a mean particle diameter of less than about 0.75 μm and preferably less than about 0.5 μm. The emulsions will be sterile and ordinarily are packaged in glass containers. They can be made by known methods. For example see U.S. Pat. No. 3,169,094 and European Patent Application No. 0071995.

The contribution of lipid to total nonprotein calories in the emulsions herein ordinarily will range about from 20% to 80%. Thus the MCTs in the emulsion will make up about from 5% to 60% of the total nonprotein calories in the emulsions, preferably about from 15% to 60%. For example in a 70 Kg man receiving 40 kcals/Kg BW/day, MCT dosage may vary about from 0.35 mg/Kg BW/min. to 2.05 mg/Kg BW/min., preferably about from 0.4 mg/Kg BW/min. to 1.00 mg/Kg BW/min. and optimally about from 0.5 to 0.75 mg/Kg BW/min. The remaining nonprotein calories are carbohydrates or a mixture of LCTs and carbohydrates.

A convenient method for preparing and administering the emulsion herein is for the hospital or user pharmacy to aseptically mix the emulsion components using commercially available equipment. The MCT and LCT emulsions are mixed with sterile aqueous solutions of other desirable additives: Amino acids in proportions suitable for disease nutrition, vitamins, carbohydrates such as dextrose, electrolytes such as potassium and sodium chloride drugs, and trace minerals such as zinc ions. The resulting product is a sterile, emulsion of MCTs and LCTs, in an aqueous solution containing amino acids in proportions characterized above, carbohydrate and, optionally, drugs, trace minerals and vitamins. Alternatively, and less preferably, the MCTs and LCTs can be mixed as oils, then emulsified and combined with the other additives noted above. Drugs which have heretofore been conventionally administered to liver disease patients (cymeditine or steroids) or septicemia patients (antibiotics) may be included in the emulsion.

The emulsions herein are packaged and stored in hermetically sealed containers for long or short term storage. The additives to be included in the emulsions will depend upon how long the emulsions are to be stored. Long term storage is acceptable for emulsions with aqueous phases containing sugar, the amino acids and some electrolytes. Dextrose should not be included in emulsions prepared for long term storage. They are administered continuously or discontinuously by infusion into the subclavian vein as is the conventional practice in total parenteral nutrition. When LCT and MCT emulsions are combined in pharmacies or are mixed with other solutions for short-term storage as discussed above they may be stored in flexible containers now available commercially for temporary storage of LCT emulsion admixtures.

The following examples are merely illustrative and are not to be considered limiting with respect to the claims. Ordinarily the emulsions are stored in glass containers.

EXAMPLE 1

In a suitable mixing vessel, 2.0 kg of MCT oil consisting of approximately 75% octanoic acid and 25% decanoic acid, 120 g of purified egg phospholipids, 225 g of glycerol, USP, and a suitable quantity of water for injection, USP, are mixed to produce a coarse emulsion. This emulsion is then homogenized repeatedly at high pressure to produce an emulsion of mean particle diameter of less than 0.75 μm. During the process, the pH of the emulsion is adjusted to a physiological range with sodium hydroxide. The final volume is adjusted, if necessary, with water for injection, USP, to 10 L and the emulsion filtered into glass containers and heat sterilized by the normal procedure.

EXAMPLE 2

To a 2 L plastic bag suitable for intravenous admixtures (Travamulsion © container) is added 385 mls of a 10% crystalline amino acid solution (Travasol 10%; Travenol Laboratories, Inc.), 535 mls of 4% isomolar branched amino acid (leucine, isoleucine, and valine) solution, 430 mls of 70% hydrous dextrose, 63 mls of 20% soybean oil emulsion (Travamulsion © 10%; Travenol Laboratories, Inc.), 217 mls of a 20% MCT oil emulsion of Example 1 and 90 mls of a solution containing appropriate electrolytes, trace minerals and vitamins. The solution is mixed by hand and is connected to an infusion pump suitable for administration into a patient. The solution contains 60 gms of amino acids and a total of 1800 kcals. 65% of the nonprotein calories are hydrous dextrose and 35% of the nonprotein calories are lipid.

The solution may be administered to a hospitalized patient over 24 hours at a constant rate of 72 mls/hr.

EXAMPLE 3

In a suitable mixing vessel, approximately 1.5 kg of MCT oil and 0.5 kg of soybean oil, 120 g of purified egg phospholipids, 225 g of glycerol, USP, and a suitable quantity of water for injection, USP, are mixed to produce a coarse emulsion. This emulsion is then homogenized repeatedly at high pressure to produce an emulsion of mean particle diameter of less than 0.75 μm. During the process the pH of the emulsion is adjusted to a physiological range with sodium hydroxide. The final volume is adjusted, if necessary with water for injection, USP, to 10 L and the emulsion filtered into glass containers and heat sterilized by the normal procedure.

EXAMPLE 4

To a 2 L container suitable for intravenous infusions of admixtures (Travamulsion © container) is added 385 mls of a crystalline amino acid solution (Travasol 10%; Travenol Laboratories, Inc.), 535 mls of 4% isomolar branched chain amino acid (leucine, isoleucine, and valine) solution, 430 mls of hydrous dextrose, 560 mls of 10% lipid emulsion comprised of 75% MCT oil and 25% soybean oil (Example 3) and 90 mls of a solution containing appropriate electrolytes, trace minerals and vitamins. The resulting solution is mixed by hand and is connected to an infusion pump suitable for administration into a patient. The solution contains 60 gms of amino acid and a total of 1800 kcals. 65% of the nonprotein calories are hydrous dextrose and 35% of the nonprotein calories are lipid in the form of a 75% MCT oil emulsion and 25% soybean oil emulsion.

The solution may be administered to a hospitalized patient over a 24-hour period at a constant rate of 72 mls/hour.

EXAMPLE 5

Hepatic insufficiency was induced in previously healthy Sprague-Dawley CR1:CD rats by portacaval anastomosis. An end-to side portacaval anastomosis (shunt) was induced by a nonsuture method using Teflon tubing. For three weeks following surgery, the rats were returned to stainless steel cages and allowed to consume laboratory chow, ad libitum. After that period in time, 24 animals were fasted overnight and hepatic function assessed by both static and dynamic indices. Results were compared to 20 similar animals that received only a sham operation.

In 12 portacaval shunted rats and 10 sham operated rats, indocyanine green clearance, an index of hepatocyte function, was evaluated.

Fifteen minutes following intravenous injection of indocyanine green, both sham operated and portacaval shunted rats were killed and results are summarized in Table 1.

TABLE 1

Portacaval Shunt (PCS) Effects of Body Weight, Liver Weight, Indocyanine Green Clearance and Serum Albumin Concentrations

| | Body Weight (g) | | Liver | Indocyanine Green | |
|---|---|---|---|---|---|
| | Before | After | Weight (g) | Retention (%) | (g/dl) |
| SHAM | 274 ± 8 | 351 ± 15 | 8.9 ± 0.6 | 9.0 ± 3.3 | 3.05 ± 0.04 |
| PCS | 277 ± 23 | 301 ± 35 | 6.2 ± 0.4* | 18.3 ± 4.7* | 2.68 ± 0.16* |

*p 0.05

Hepatic dysfunction was clearly evident. Liver weight in portacaval shunted rats was 42% less than in sham operated animals (p 0.05) and serum albumin concentration (a liver synthesized protein) was also significantly reduced (p 0.05). As a dynamic assessment of hepatocyte function, indocyanine green retention was almost twice as great (p 0.05) in portacaval shunted rats indicating reduced clearance.

In addition to these assessments, hepatic reticuloendothelial system function was evaluated in 12 additional portacaval shunted rats and 10 sham operated rats. The blood concentration of live *Pseudomonas aeruginosa* P4 in portacaval shunted rats following an intravenous challenge of $5 \times 10^8$ cfu of bacteria was about ten times greater (one log) than the sham operated group (Table 2) (p 0.05). Although the capacity to clear bacteria was reduced in portacaval shunted rats, the capacity of the spleens to sequester Pseudomonas was markedly increased, indicating a compensatory role by that organ.

TABLE 2

Effect of PCS on Host Nonspecific Immunity and Organ Reticuloendothelial System Function

| | Blood Bacteremia (log conc.) | | | Organ Sequestration (%) | |
|---|---|---|---|---|---|
| | 0° | 30° | 60° | Liver | Spleen |
| SHAM | 7 | 4.5 ± 0.3 | 3.0 ± 0.3 | 35 ± 2 | 6 ± 1 |
| PCS | 7 | 5.4 ± 0.2* | 4.2 ± 0.2* | 38 ± 2 | 12 ± 1 |

*p 0.05

Therefore, the portacaval shunt model in the rat produced a hepatic insufficiency model which mimics in many ways the clinical conditions seen in human liver disease.

Twenty-eight male Sprague-Dawley CR1:CD rats underwent portacaval anastomosis and splenectomy and were returned to their metabolic units for 3 weeks. Following the recovery period, the rats were randomized to receive total parenteral nutrition for four days. All of the diets delivered 300 kcals/Kg BW/day and 12.5 g amino acid/day except for the dextrose only group ("D only") which received only 300 dextrose kcals/Kg BW/day. One group of animals received all of the nonprotein calories as dextrose (AA+D) whereas the remaining two groups received half of their nonprotein calories as lipid. One of the lipid groups received its fat calories as a soybean (LCT) oil emulsion (AA+D+L) while the remaining lipid group received one-half of the fat calories as the 20% MCT oil emulsion of example 1 and the other half as a 20% soybean oil emulsion (AA+D+PM).

TABLE 3

Protein Responses to Various TPN Regimens in Portocaval Shunted Rats.

| | Serum Albumin | Fractional Synthetic Rate (%/d) | | N Balance |
|---|---|---|---|---|
| | (g/dl) | Albumin | Muscle | (mg/4 days) |
| AA + D + PM | 3.2 ± 0.3* | 85 ± 14 | 5.7 ± 2.2 | 61 ± 14 |
| AA + D + LCT | 3.0 ± 0.5 | 84 ± 15 | 6.1 ± 1.2 | 20 ± 35 |
| AA + D | 2.6 ± 0.3 | 68 ± 5 | 5.9 ± 1.0 | 71 ± 32 |
| D only | 2.4 ± 0.5 | 20 ± 8* | 5.6 ± 2.8 | −150 ± 10* |

*p 0.05 vs AA + D

Results summarized in Table 3 demonstrated that portacaval shunted rats given the 50:50 physical mixture (PM) of MCT emulsion and soybean oil emulsion had the highest serum level of albumin (a hepatic secretory protein), and serum albumin levels were lowest in animals given only glucose. In addition, liver histology (following hemotoxylin and eosin staining) showed marked infiltration of glycogen in the hepatocytes from rats infused with dextrose regimens (AA+D and D only). In contrast, in rats given all of their nonprotein calories as a soybean oil emulsion and glucose (Group AA+D+LCT) increased lipid sequestration in the Kupffer cells was observed. Rats given nonprotein calories as glucose and the physical mix of soybean and MCT oil emulsion (AA+D+PM) had normal hepatic physiology.

The improved liver morphology and albumin concentration in the rats given the 50:50 physical mix of soybean oil emulsion and MCT oil emulsion support the conclusion that MCTs as a component of total parenteral nutrition are an effective energy source during hepatic dysfunction.

The effect of MCT emulsions on reticuloendothelial system function was investigated in 24 additional portacaval shunted rats that had also undergone splenectomy. Seven weeks following portacaval anastomosis and splenectomy, all animals received diets that delivered 200 kcals/Kg BW/day and 8.3 g amino acid/Kg BW/day. Lipid was given at 50% of the total nonprotein calorie intake as either a 10% soybean oil emulsion (AA+D+LCT) or a 10% MCT oil emulsion (AA+D+MCT). To assess reticuloendothelial system function following these courses of total parenteral nutrition, a body weight-related dose of $E.\ coli$ was administered intravenously.

TABLE 4

| | Effect of MCT AND LCT on Reticuloendothelial System Function in PCS Rats | | | | | |
|---|---|---|---|---|---|---|
| | N Balance | Blood Bacteria (log conc) | | | Organ Sequestration (%) | |
| | (mg/5d) | 0° | 30° | 60° | Liver | Lung |
| SHAM + AA + D + LCT | 117 + 15 | 7 | 4.2 ± 0.4* | 3.4 ± 0.2 | 36.4 ± 1.2 | 12.5 ± 1.2 |
| PCS + AA + D + LCT | 101 + 38 | 7 | 5.5 ± 0.3 | 4.8 ± 0.2 | 42.1 ± 2.3 | 15.5 ± 2.0 |
| PCS + AA + D + MCT | 105 + 18 | 7 | 4.5 ± 0.1* | 3.9 ± 0.2* | 55.7 ± 4.5* | 8.4 + 0.7* |

*p 0.05 vs PCS + AA + D + LCT

No differences in nitrogen balance were observed (Table 4). However, decreased bacterial clearance and liver uptake of $E.\ coli$ indicative of hepatic reticuloendothelial system blockade were seen in portacaval shunted and splenectomized rats given lipid calories as a soybean oil emulsion. Such results suggest that administration of LCT oil emulsions without MCTs may have adverse effects during hepatic insufficiency. In contrast, intravenous MCT emulsions support nitrogen balance equally well and may better support hepatic reticuloendothelial system function in order to improve sequestration of organisms in the liver during bacteremia.

EXAMPLE 6

This contemplated example demonstrates the use of an MCT emulsion in providing parenteral nutrition to a liver diseased patient.

A 47-year-old white male (62 Kg) is admitted to the hospital because of delirium and hematemesis. The patient had a 25 year history of alcohol abuse and on a previous admission had biopsy proven alcoholic cirrhosis. Gastroscopy had demonstrated the presence of extensive esophageal varices.

Laboratory analysis of the patient confirmed the clinical diagnosis of variceal bleeding secondary to decompensated alcoholic cirrhosis. Total bilirubin was 7 mg/dl (normal less than 1 mg/dl); serum glutamate-oxalo-acetate transaminase was 80 U/L (normal less than 15 U/L). Serum glutamate pyruvate transaminase was 155 U/L (normal less than 15 U/L) and serum gamma glutaryl transaminase was 180 U/L (normal less than 30 U/L). Hemoglobin was 7.5 g/l (normal=14-16 g/l).

Serum albumin concentration was 1.9 g/dl (normal greater than 3.5 g/dl) and total protein 4.4 g/dl (normal greater than 6 g/dl) reflecting visceral protein attrition.

Abnormalities in the serum amino acid pattern were also evident with L-tyrosine being 274 nmols/ml (normal 50-100 nmols/ml) and L-phenylalanine being 332 nmols/ml (normal 50-100 nmols/ml). The serum aromatic to branched chain amino acid ratio was 2.74 with normal being less than 0.80.

The patient's mental condition varied from Grade II to Grade III coma and the patient had severe asterixis. During the first two days of admission, 2 gms of neomycin, twice daily, and 20 mls of 10% lactulose three times daily, were administered. Due to acute alcohol withdrawal, the patient's clinical course was complicated by the presence of alcohol-induced delirium tremens.

Because of the patient's reduced visceral protein status, nutritional support was recommended. Oral intake was not recommended because of the decreased mental status and presence of delirium tremens. Use of nasogastric feeding tube was also contraindicated because of esophageal varices. The physicians recommended total intravenous nutrition and a subclavian catheter was inserted into the superior vena cava.

Nutritional support for the patient was set at a total calorie intake of 30 kcals/Kg BW/day and protein (as amino acid equivalents) at 1.0 g/Kg BW/day. The amino acid source was a standard amino acid mixture (Travasol amino acids) supplemented with the branched chain amino acids, leucine, isoleucine, and valine so that the total branched chain proportion was 50% of the total amino acids by weight.

The remaining 26 kcals/Kg BW/day were administered as 65% hydrous glucose and 35% as a physical mixture of 20% MCT oil emulsion and 20% soybean oil emulsion. 75% of the lipid calories were given as the medium chain triglyceride oil emulsion and 25% of the lipid calories as a soybean oil emulsion. Actual daily intake of the hydrous glucose was 3.5 mg/Kg/min, of the soybean oil emulsion was 0.174 mg/Kg/min and of the MCT oil emulsion, 0.585 mg/Kg/min. Electrolytes, trace minerals, and vitamins were adjusted daily to meet the established requirements of the patient.

The entire formula was administered in a course of therapy commencing with 1720 ml of fluid continuously over a 24 hour period at a rate of 72 mls/hr through the subclavian vein catheter. The patient's condition was considered to have improved after treatment with the regimen of this Example.

EXAMPLE 7

The impact lipid emulsions have on host defense against bacterial infection during total parenteral nutrition (TPN) was measured by two studies. In study I, the experimental model of bilateral hind limb fractures and $E.\ coli$ bacteremia was evaluated for the presence of systemic bacteremia and pyrexia. In study II, the effect of different total parenteral nutrition regimens containing dextrose and LCT and/or MCT emulsions was evaluated in these injured/infected animals.

Study I—Under diethyl ether anesthesia, six previously healthy male sprague-Dawley CD rats (300-325 gms) received a 2 cm abdominal incision and a low frequency radiotransmitter capable of measuring temperature (Minimitter Model M, Minimitter Co., Sun River, Oreg.) was implanted into the peritoneal cavity. The abdominal would was closed and the animals were subjected to bilateral hindlimb fractures. Briefly, the hindlimbs were shaved and a small skin incision (2 cm), was made on the lateral aspect of the upper quadrant of each hindlimb. The femur of each leg was exposed by blunt dissection and the femurs were fractured with sterile forceps. The fractured femurs were then packed with 1 cm$^2$ of gauze which had been previously cultured for 12 hours in thioglycolate media with *Escherichia coli*. The wounds were closed and the animals were returned to their metabolic cages.

For the next three days, body temperature was recorded every 15 minutes. At daily intervals, blood bacteremia levels were measured in all animals. Venous blood, 0.025 mls, was obtained by accessing the ocular venous plexus via a lateral approach with a heparinized capillary tube. Colony counts and characterization of the pathogen were confirmed by serial dilutions and plating on horse blood-agar dishes.

Study II—52 male Sprague-Dawley CD rats (Charles River Breeding Laboratories, Wilmington, Mass.) were maintained in individual cages in a light-controlled room at an ambient temperature of 26° C. For five days, all animals were fed a stock laboratory diet (Charles River D-3000, Agway Agricultural Products, Minneapolis, Minn.) and tapwater ad libitum. During this period, *E. coli* cultures were grown for 12 hrs in culture vials which contained 3% trypticase soy broth in an incubator at a constant temperature of 37° C. To these cultures were added sterile sections of cotton gauze (1 cm$^2$).

After the animals had exhibited adequate weight gain, rats weighing 280-300 gm received a 0.025"×0.041" Silastic catheter (Dow-Corning Labs., Corning, N.Y.), inserted via the internal jugular vein and advanced to the superior vena cava, under diethyl ether anesthesia (38). The catheter was attached to a flow-through swivel (Instech lab., Philadelphia, Pa.) that allowed continuous infusion of solutions and free movement of the animals.

Following this procedure, animals were randomly divided into three groups and placed on total parenteral nutrition regimens. These solutions delivered approximately (250 kcal/kgBW/day) and were isonitrogenous (12.5 g AA/kgBW/day). Group I received 200 kcal/kgBW/day of dextrose. Group 2 and 3 received 50% of the non-protein calories a fat. Group 2 was given 100 kcal/kgBW/day of long chain triglyceride (LCT) emulsion (20% Travamulsion, Travenol Laboratories Inc., Deerfield, Ill.). Group 3 received 100 kcal of a lipid emulsion containing 75% medium chain triglycerides (20% MCT, Travenol Laboratories Inc., Deerfield, Ill.) and 25% long chain triglycerides (75% MCT/25% LCT). Animals were infused at a rate of 72 ml/day (Table 1). Twenty-four hours following the start of TPN, all animals were reanesthetized with diethyl ether and bilateral femur fractures were performed as previously described. The wounds were closed with 4.0 Ethilon monofilament nylon sutures (Ethicon, Inc., Somerville, N.J. 08876) and the animals were returned to their cages. TPN was continued for an additional three days. During this period, urine was collected for determination of nitrogen balance and the bottles containing the intravenous solutions were changed daily.

At the end of the three days, the animals were given an intraperitoneal injection of sodium pentobarbital (20 mg/kgBW). The inner hind limb was shaved and the femoral artery was exposed. Into this vessel, a 2-3 cm piece of Intramedic polyethylene tubing (No. 7400, Clay Adams, Parsippany, N.J.) was inserted in order to determine blood bacteria concentrations. At time zero, a weight related dose ($1\times10^7$ cfu/gm BW) of *E. coli* radiolabelled with $^{59}$Fe-citrate was introduced via the jugular catheter.

Immediately before and following intravenous challenge with radiolabelled *E. coli*, 0.5 ml of blood were withdrawn from the arterial lines and bacterial colony counts were determined (15, 30 and 60 min.). At 60 minutes, the animals were sacrificed to determine the uptake of $^{59}$Fe-labelled bacteria in the organs of the reticuloendothelial system (RES).

Analytical Methods

*Escherichia coli* bacteremia—A variation of the method of Hosia et al for studying blood clearance was used. At time 0, after obtaining baseline bacteria levels, a weight-related quantity of *Escherichia coli* 075 sufficient to produce an initial bacteremia of $1\times10^8$ cfu/ml of blood was injected into the jugular vein of the animals. These bacteria had been previously radiolabelled by adding 50 uCi of $^{59}$Fe-citrate (ICN Biochemicals, Irvine, Calif.) to a Trypticase soy broth 12 hrs before administration. Incorporation of the 59Fe-citrate into the *E. coli* occurred during log-phase growth of the bacteria and was confirmed by washing the cells three times with sterile physiologic saline until all radioactivity was associated with the bacteria and not the medium.

At 15, 30 and 60 minutes following initial injection, 0.5 ml blood was collected from the anesthetized animals via the femoral artery catheter. Standard serial dilutions were performed and replicates were plated on horse blood-agar plates for overnight incubation at 37° C.

Organ Sequestration—60 minutes following injection of labelled bacteria, all animals were sacrificed by decapitation., Organs of the RES, (ie. the liver, lung and spleen) were removed and radioactivity was measured in a Beckman Gamma Counter (model #4000; Irvine, Calif.).

Nitrogen Balance—Urine was measured and collected over the three day period during TPN feeding in flaskes containing 1 ml of 30% HCL. Urinary nitrogen was measured spectrophotometrically on an automated analyzer following micro-Kjeldhal digestion.

Statistical Analysis—Data are presented as mean +—SEM for each group and were analyzed on an IBM PC with Northwest Analytical Statistical Package (Portland, Oreg.). If significance was obtained by one way analysis of variance, the inter-group comparisons were determined by a Student's two-tailed t-test. Significance was designated at the 95% confidence level.

Results

Study I—FIG. 1 represents the change in body temperature from baseline of the control rats following bilateral hindlimb fractures and *E. coli* infection. Within 12 hours, body temperature increased by 1.5°-2.0° C. and was elevated over the entire 72 hour period. However, body temperature did tend to decline after the zenith was reached at approximately 24 hours.

Figure 2:
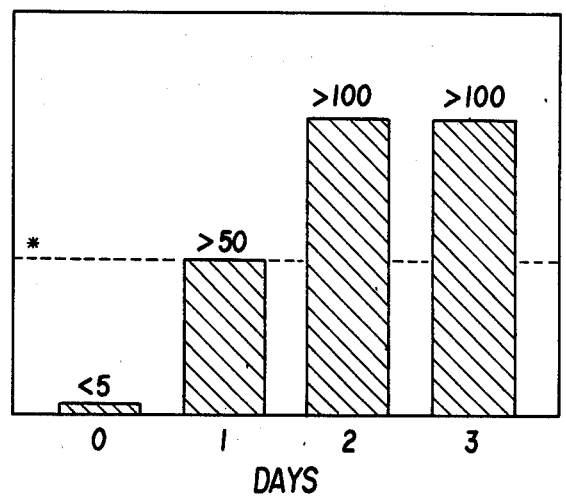
FIG. 2 relates to example 7 and illustrates the blood bacteremia for the control rats of Study I.

In addition, by the 24th hour following the injury/infection, all of the animals were bacteremic (FIG. 2). In every case, greater than 100 cfu/ml of blood were observed and, in the majority of the samples, *E. coli* were isolated from blood. Occasional colonies of Enterobacter and *Staphylococcus aureus* were also observed.

Figure 3:
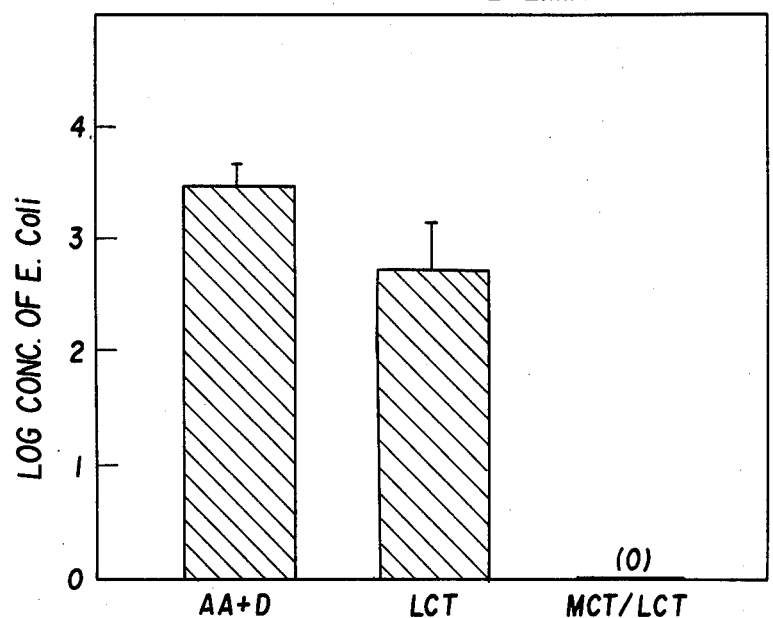
FIG. 3 relates to example 7 and illustrates the baseline bacteremia of the rats of Study II.

Study II—FIG. 3 represents the baseline bacteremia observed in the three groups of rats receiving parenteral nutrition and following the hindlimb fractures. Rats receiving either glucose as the only calorie source or LCT were bacteremic following the bilateral hindlimb fractures and three days of TPN (AA+G=3.49±0.22 cfu/ml, LCT=2.72 ±0.62 dfu/ml). Only the group given MCT as part of their nonprotein calorie source exhibited no baseline bacteremia.

Figure 4:
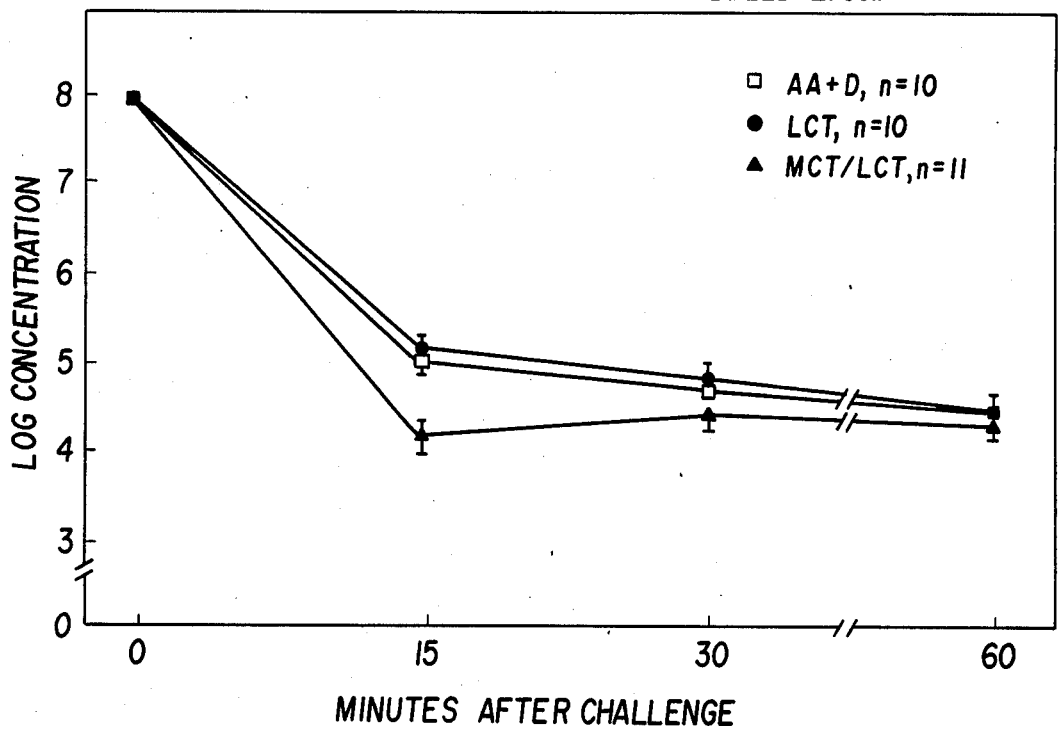
FIG. 4 relates to example 7 and illustrates the bacterial log concentrations in the rats of Study II.

FIG. 4 represents the bacterial log concentrations in the blood of the animals at 15, 30 and 60 minutes following intravenous challenge with labelled bacteria. Data are presented as the number of colony forming units (cfu/ml) of blood versus time. There was a trend in the group given an MCT containing lipid infusion to have less bacteria in their blood; however, this was not statistically significant.

Figure 5:
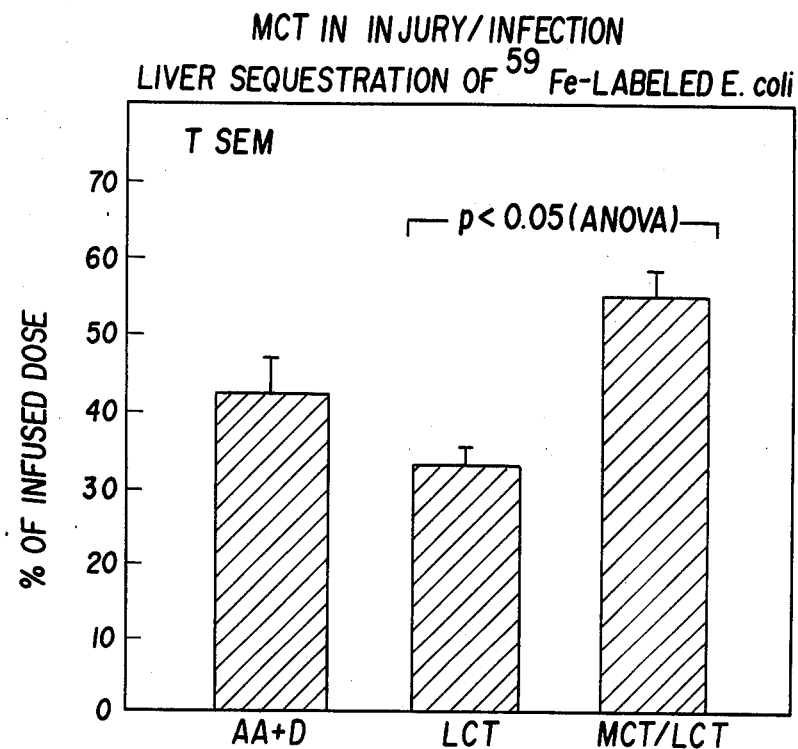
FIG. 5 relates to example 7 and illustrates the proportion of radioactive labelled bacteria sequestered by the liver of the rats of Study II.
Figure 6:
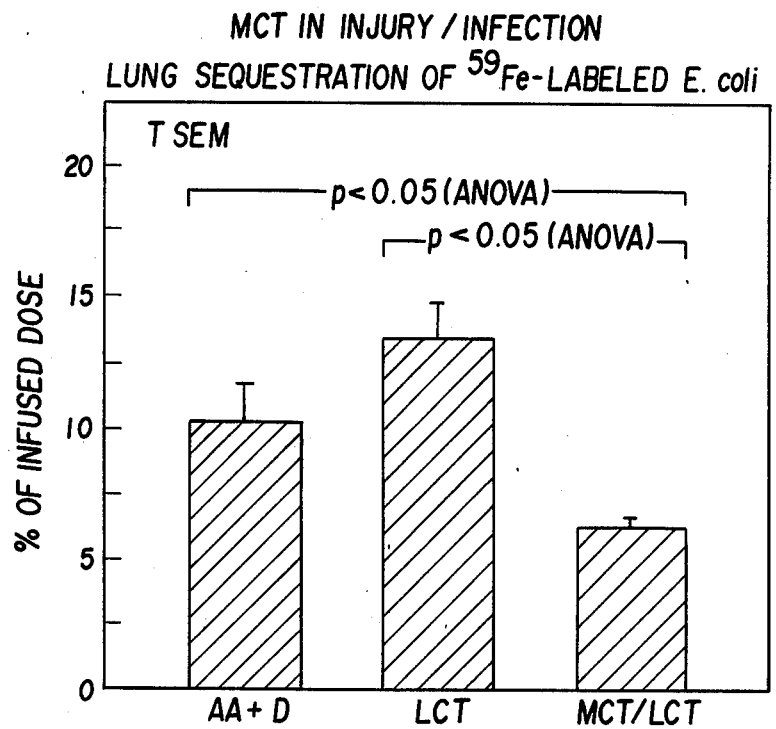
FIG. 6 relates to example 7 and illustrates the amount of bacteria deposited in the lungs of the rats of Study II 60 minutes following I.V. challenge with radiolabelled bacteria.
Figure 7:
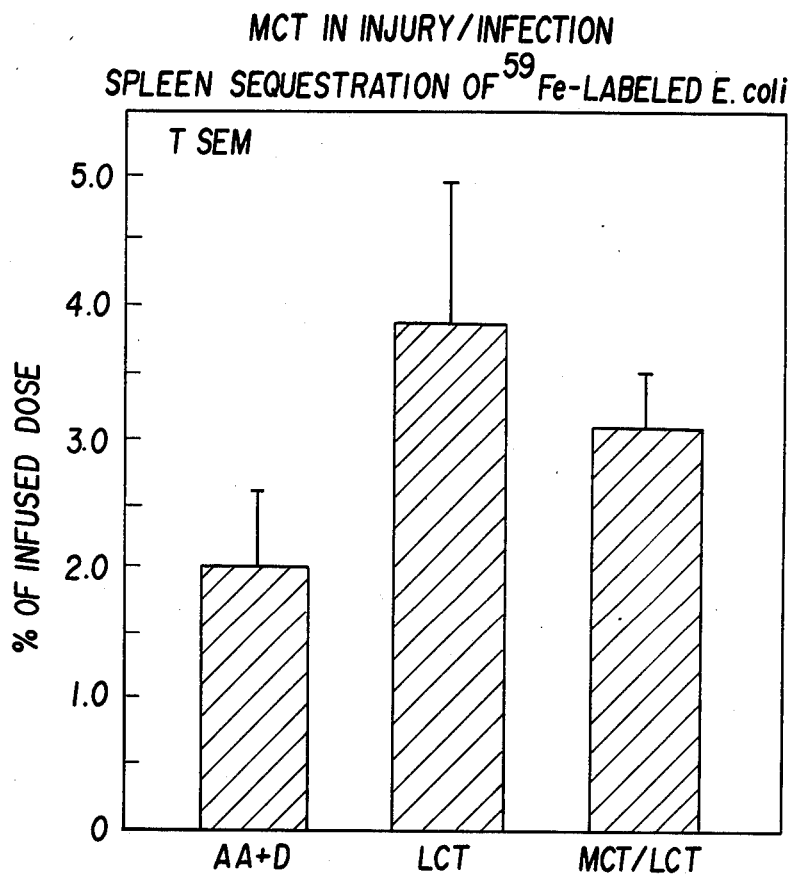
FIG. 7 relates to example 7 and illustrates the splenic uptake of E. coli by the rats of Study II.

The organ sequestration of $^{59}$Fe-radiolabelled bacteria is presented in FIGS. 5-7. FIG. 5 shows the proportion of radioactive labelled bacteria sequestered by the liver. Animals given MCT as part of TPN were able to sequester significantly (55.37±4.21%) ($p<0.05$) more bacteria when compared to the group given LCT (33.21±3.59). The animals given the mixed LCT-glucose fuel system and the glucose only group sequestered similar amounts of bacteria in the liver, which was approximately 30% less than the animals on a mixed MCT-LCT-glucose system.

FIG. 6 shows the amount of bacteria deposited in the lungs 60 minutes following I.V. challenge of radiolabelled bacteria. MCT fed rats sequestered the least amount of bacteria when compared to the other two group (MCT=6.17±0.74% vs LCT=13.45±1.65% and AA+G=10.27±1.54% ($p<0.05$). Although significance was not reached with the numbers of animals studied, there was a tendency for the group given the LCT alone (Group 2) to have more bacteria deposited in their lungs compared to the group given glucose alone (Group 1).

Figure 8:
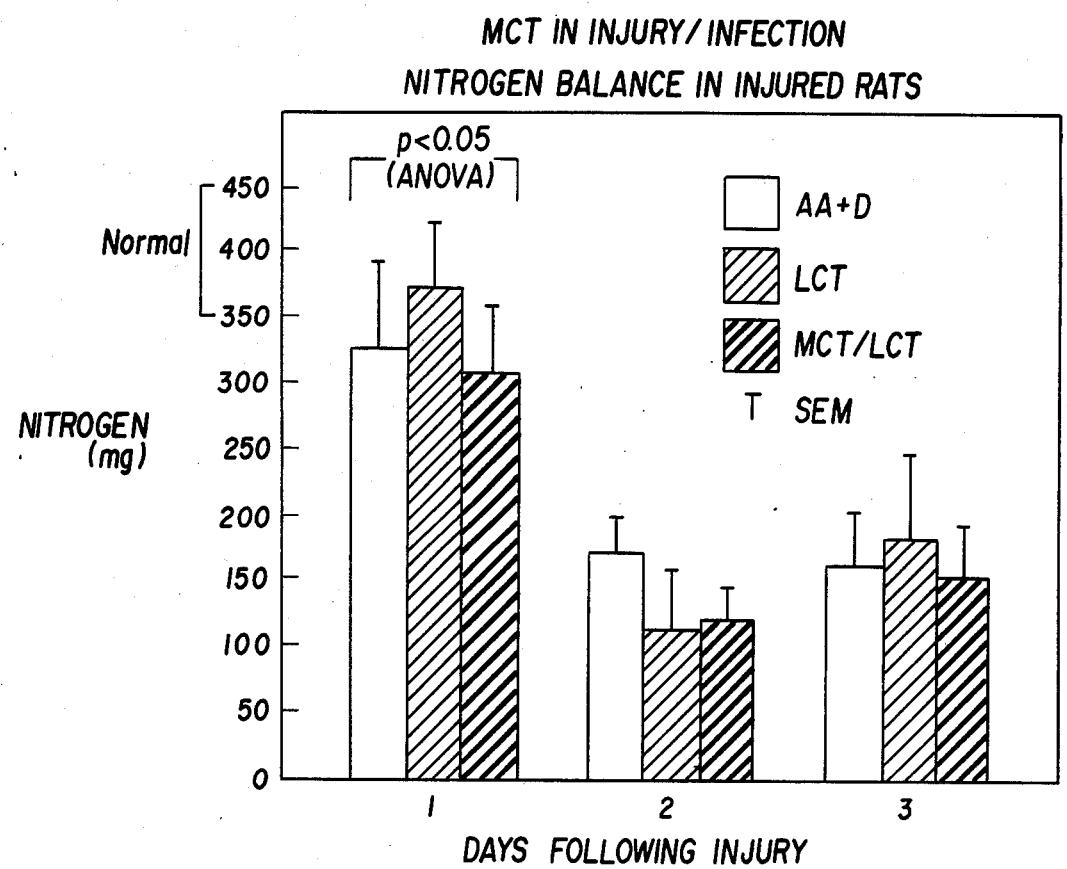
FIG. 8 relates to example 7 and illustrats the daily nitrogen balance of the rats of Study II.

There was no difference in splenic uptake of *E. coli* (FIG. 7) or in the daily nitrogen balance (FIG. 8) among the three groups. However, there was a significant drop in nitrogen balance over the three days following the injury/infection. Overall mortality following the onset of infection was greater than 40%, yet there was no difference in survival among the three groups.

DISCUSSION

Nutritional support of the bacterially-infected patient is aimed at reducing the loss of lean tissue and supporting host immunologic function. Yet at present, no consensus exists regarding the optimal parenteral regimen for the infected or septic patient.

Complications associated with all carbohydrate TPN regimens include an obligatory hepatic lipogenesis with increased carbon dioxide production, cholestasis, reduced hepatic protein synthesis and decreases in lung surfactant production. Some investigators have suggested that a portion of the carbohydrate calories be replaced with commonly available lipid emulsions, comprised predominantly of long triglycerides. These investigators have suggested that such mixed fuel systems reduce the risk of developing fatty livers, decrease carbon dioxide production and improve hepatic secretory protein syntheses.

Unfortunately, excessive or prolonged administration of currently available long chain triglyceride emulsions is also associated with complications. Autopsy examinations from critically ill patients who have received soybean oil emulsions show considerable deposition of milky white clotted clumps of lipid in the heart, kidney and lungs. Recent studies by Goodenough and colleagues reveal that approximately 8% of administered long chain triglyceride emulsions are immediately oxidized and the remainder are retained in the body as neutral fats.

In vitro studies in humans have also shown impaired leukocyte chemotaxis and random migration and further reductions in bactericidal capacity when incubated with physiologic levels of lipid emulsion. More importantly, studies have revealed that current long chain triglyceride emulsions, when given as the principal calorie source, reduce reticuloendothelial system function and increase bacterial sequestion in the lungs.

The current study was undertaken to determine the effect of different total parenteral nutrition regimens on nitrogen balance and nonspecific host defense in an injured and infected animal model. Rats were subjected to bilateral hindlimb fractures with *E. coli*-induced sepsis. As shown in FIGS. 1 and 2, this model resulted in a systemic bacteremia and a reproducible febrile state. Although hemodynamic data was not obtained, the bacteremia and maintenance of a febrile state over the entire 72 hour period, suggests that these animals were in a hyperdynamic, septic condition.

The overall motality rate in this study was greater than 40% indicating a semi-lethal infection. Although this study was not designed to investigate the effect of the three nutrient regimens on overall survival, the response by the survivors to a subsequent *E. coli* intravenous challenge markedly differed. Initially, animals receiving either an all-glucose TPN regimen or a mixed fuel system in which long chain triglycerides were the sole lipid source had a marked bacteremia ($10^2$-$10^4$ cfu/ml). In contrast, rats receiving the TPN formula comprised of 75% MCT and 25% LCT were not bacteremic after three days of TPN.

The differences in baseline bacteremia can be explained, in part by reticuloendothelial system function in these animals. Although MCT-fed rats did not clear an i.v. challenge of *E. coli* significantly more rapidly than animals receiving all-glucose or LCT-based TPN, the pattern of organ sequestration differed. Rats given the LCT-based parenteral nutrition sequestered fewer bacteria in the liver than the animals receiving the mixed MCT-LCT system.

Of particular interest was the increased sequestration of bacteria in the lungs of rats administered long chain triglyceride. In contrast, all-glucose regimens or formulations with large quantities of MCT do not contain significant quantities of precursors for prostaglandin production and may not exacerbate an already activated pulmonary macrophage system. Such MCT-containing regimens bay be beneficial during sepsis when the lung is especially susceptible to secondary infection.

These findings demonstrate that the response by a septic organism to various nutritional regimens depends upon the presence and type of lipid emulsion administered. Despite similar preservation of body nitrogen with all three regimens, host immunity can be adversely affected or uniquely supported depending upon the nutritional regimen used.

We claim:

1. A method of treating septicemia comprising parenterally administering a composition including MCT's and LCT's to a patient with septicemia, the proportion of MCT's to LCT's ranging about from 1:3 to 3:1.

2. The method of claim 1 wherein the patient has an active infection.

3. The method of claim 2 wherein greater than 0.35 mg MCT/LCT's per kilogram of body weight per minute are administered to said patient.

4. A sterile composition for treating septicemia comprising an emulsion of MCT's and LCT's in the proportion ranging from about 1:3 to 3:1, respectively.

* * * * *